United States Patent
Ikemoto

(10) Patent No.: US 7,822,248 B2
(45) Date of Patent: Oct. 26, 2010

(54) ENDOSCOPE PROCESSOR, COMPUTER PROGRAM PRODUCT, AND ENDOSCOPE SYSTEM

(75) Inventor: Yosuke Ikemoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 808 days.

(21) Appl. No.: 11/748,702

(22) Filed: May 15, 2007

(65) Prior Publication Data
US 2007/0269088 A1 Nov. 22, 2007

(30) Foreign Application Priority Data
May 16, 2006 (JP) ............... 2006-136691

(51) Int. Cl.
*G06K 9/00* (2006.01)
(52) U.S. Cl. .............. 382/128; 382/100; 382/130; 382/131; 600/178; 600/180; 600/181; 600/476; 600/160; 348/70; 348/71; 348/73
(58) Field of Classification Search ............... 382/128, 382/100, 131, 130; 348/70, 71, 73; 600/476, 600/160, 178, 180, 181; 250/458.4, 461.1
See application file for complete search history.

(56) References Cited

U.S. PATENT DOCUMENTS

| | | | |
|---|---|---|---|
| 6,418,245 B1 * | 7/2002 | Udagawa | 382/312 |
| 6,879,339 B2 * | 4/2005 | Ozawa | 348/71 |
| 6,967,673 B2 | 11/2005 | Ozawa et al. | |
| 7,050,086 B2 | 5/2006 | Ozawa | |
| 7,636,464 B2 * | 12/2009 | Kobayashi et al. | 382/128 |
| 7,728,867 B2 * | 6/2010 | Fukuyama et al. | 348/65 |
| 2002/0008769 A1 * | 1/2002 | Sato | 348/333.05 |
| 2004/0160519 A1 * | 8/2004 | Horita | 348/234 |
| 2006/0170942 A1 * | 8/2006 | Chiba | 358/1.9 |
| 2006/0211917 A1 | 9/2006 | Ikemoto et al. | |
| 2010/0033597 A1 * | 2/2010 | Ikemoto et al. | 348/229.1 |

OTHER PUBLICATIONS

U.S. Appl. No. 11/748,684 to Ikemoto, filed May 15, 2007.

* cited by examiner

*Primary Examiner*—Wes Tucker
*Assistant Examiner*—Nancy Bitar
(74) *Attorney, Agent, or Firm*—Greenblum & Bernstein, P.L.C.

(57) ABSTRACT

An endoscope processor comprising a signal receiver and a standard value calculator is provided. The signal receiver receives an image signal generated based on an optical image captured at a light receiving surface on an imaging device. The image signal comprises a plurality of pixel signals generated by a plurality of pixels according to amounts of received light. A plurality of the pixels are arranged on the light receiving surface. The standard value calculator calculates a standard value using a focused pixel signal and surrounding pixel signals. The surrounding pixel signals are the pixel signals of surrounding pixels. The surrounding pixels surround the focused pixel. The standard value is used for carrying out signal processing on the focused pixel signal.

8 Claims, 6 Drawing Sheets

ENDOSCOPE PROCESSOR, COMPUTER PROGRAM PRODUCT, AND ENDOSCOPE SYSTEM

BACKGROUND OF THE INVENTION

1. Field of the Invention

The present invention relates to image signal processing that enables a user to discriminate a desired object from an entire image captured with an electronic endoscope.

2. Description of the Related Art

An electronic endoscope, having an imaging device at the end of an insertion tube, is used for medical examinations, industrial examinations, and so on. Light is irradiated from the end of the insertion tube to illuminate an object for observation. An optical image formed by the reflected light is captured by the imaging device, and the captured image is displayed on a monitor.

A medical endoscope is used for identifying abnormal tissue or a lesion of internal organs. The appearance of abnormal tissue or a lesion is different from that of healthy tissue. Based on the user's observation, the abnormal tissue or lesion can be identified.

However, the outer appearance of a lesion that exists deep under the surface of an organ is not clearly defined from that of healthy tissue. Therefore, it is often difficult to distinguish such a lesion.

SUMMARY OF THE INVENTION

Therefore, an object of the present invention is to provide an endoscope processor that carries out signal processing on the image signal generated by an electronic endoscope in order that a lesion is easily distinguishable from a displayed image which corresponds to the image signal.

According to the present invention, an endoscope processor comprising a signal receiver and a standard value calculator is provided. The signal receiver receives an image signal. The image signal is generated based on an optical image captured at a light receiving surface on an imaging device. The image signal comprises a plurality of pixel signals. The pixel signals are generated by a plurality of pixels according to amounts of received light. A plurality of the pixels are arranged on the light receiving surface on the imaging device. The standard value calculator calculates a standard value using a focused pixel signal and surrounding pixel signals. The focused pixel signal is the pixel signal of a focused pixel. The surrounding pixel signals are the pixel signals of surrounding pixels. The focused pixel is each pixel designated one by one. The surrounding pixels surround the focused pixel. The standard value is used for carrying out signal processing on the focused pixel signal.

Further, the endoscope processor comprises a signal processor. The signal processor calculates a signal difference value and an emphasized value, and converts the image signal into an emphasized image signal. The signal difference value is the difference between the signal level of the focused pixel signal and the standard value. The emphasized value is calculated by multiplying the signal difference value by a predetermined gain. The image signal is converted into the emphasized image signal by replacing the focused pixel signal with a signal corresponding to the sum of the standard value and the emphasized value. The standard value is the average of the signal levels to the focused pixel signal and the surrounding pixel signals.

Further, the endoscope processor comprises a signal processor. The signal processor converts the image signal into an emphasized image signal by converting original gradations of the pixel signal into converted gradations based on the standard value. The original gradations is greater than $2^n$. The converted gradations is $2^n$. The standard value is the average of the signal levels of the focused pixel signal and the surrounding pixel signals.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
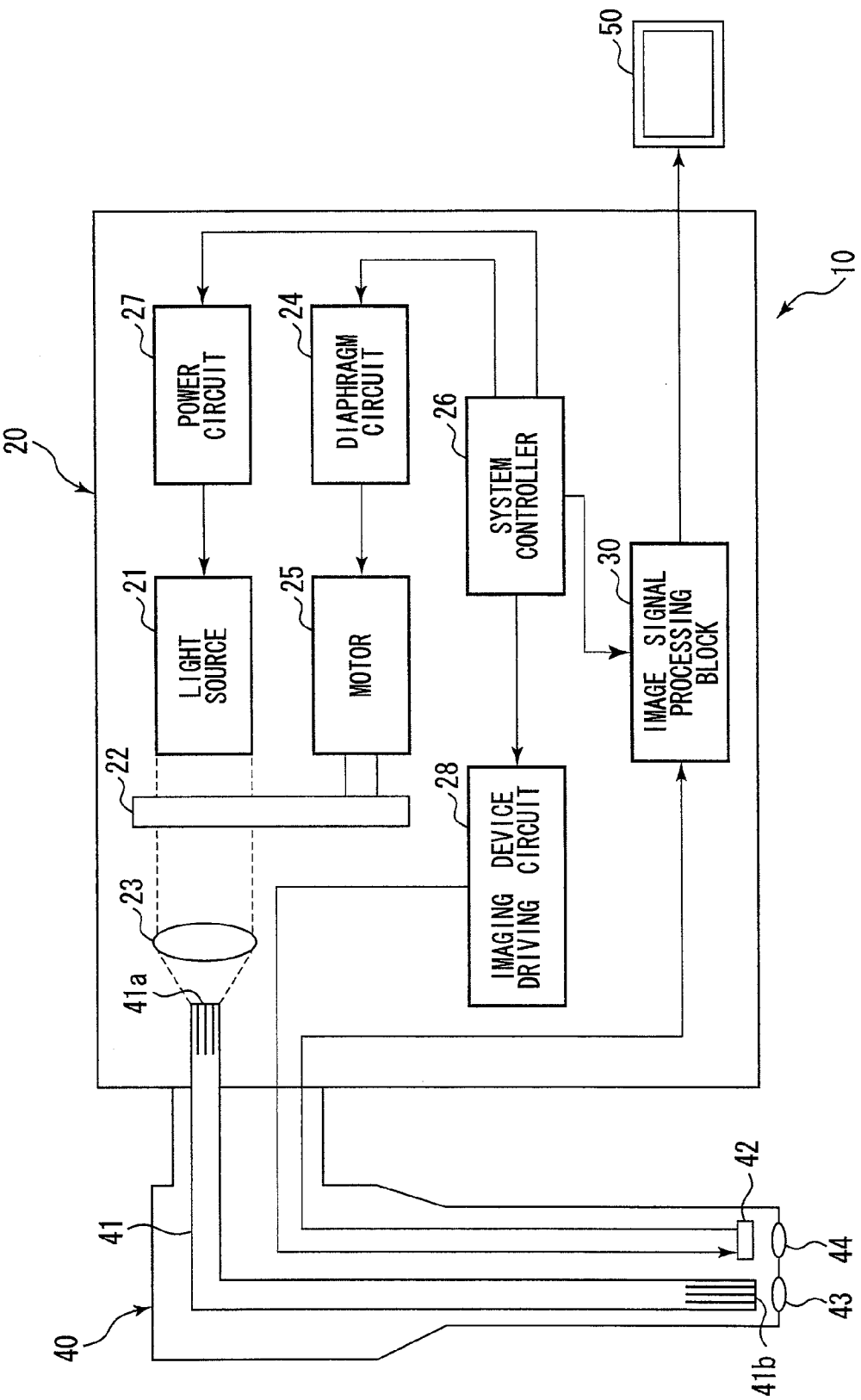
FIG. 1 is a block diagram showing the internal structure of an endoscope system having an endoscope processor as a first embodiment of the present invention.

The present invention is described below with reference to the embodiments shown in the drawings.

In FIG. 1, an endoscope system 10 comprises an endoscope processor 20, an electronic endoscope 40, and a monitor 50. The endoscope processor 20 is connected to the electronic endoscope 40 and the monitor 50 via connectors (not depicted).

The whole structure of the endoscope system 10 is briefly explained. A light source 21 for illuminating an object (not depicted) is housed in the endoscope processor 20. The light emitted from the light source 21 is irradiated onto an object (not depicted) via a light guide 41 housed in the electronic endoscope 40.

An imaging device 42, such as a CCD image sensor, is mounted in the electronic endoscope 40. The image of an object which is irradiated by the illumination light is captured by the imaging device 42. Subsequently, an image signal corresponding to the image of the captured object is generated by the imaging device 42. The image signal is sent to the endoscope processor 20, where predetermined signal processing is carried out on the image signal. The image signal, having undergone the predetermined signal processing, is converted into a composite video signal and sent to the monitor 50, where the resulting image is displayed.

Next, each component of the endoscope system 10 is explained in detail, as follows: A diaphragm 22 and a condenser lens 23 are mounted in the optical path from the light source 21 to the incident end 41a of the light guide 41. The light, which is composed almost entirely of parallel light beams emitted by the light source 21, is made incident on and condensed onto the incident end 41a by the condenser lens 23.

The intensity of the light, made incident on the incident end 41a, is controlled by adjusting the diaphragm 22. The diaphragm 22 is adjusted by a motor 25. The movement of the motor 25 is controlled by the diaphragm circuit 24. The diaphragm circuit 24 is connected to an image signal processing block 30 via a system controller 26. The image signal processing block 30 detects the magnitude of light received in the captured image of an object based on the image signal generated by the imaging device 42. The diaphragm circuit 24 calculates the necessary degree of adjustment for the motor 25 based on the magnitude of light received.

A power circuit 27, which supplies power to the light source 21, is electrically connected to the system controller 26. A control signal for switching the light source 21 on and off is output from the system controller 26 to the power circuit 27. Consequently, the lighting status (on and off) of the light source 21 is controlled by the system controller 26.

Further, the system controller 26 outputs a driving signal necessary for driving the imaging device 42, to an imaging device driving circuit 28. The imaging device 42, which is driven by the imaging device driving circuit 28, generates an image signal corresponding to the captured image of an object.

Further, the system controller 26 controls the activity of the whole endoscope processor 20. An image signal processing block 30 is also controlled by the system controller 26, as described later.

The light made incident on the incident end 41a is transmitted to the exit end 41b via the light guide 41. The transmitted light illuminates a peripheral area around the head end of the insertion tube of the electronic endoscope 40 after passing through a diffuser lens 43. An optical image of the illuminated object is focused onto the light receiving surface of the imaging device 42 by an object lens 44.

A plurality of pixels (not depicted) is arranged in two dimensions on the light receiving surface of the imaging device 42. Each pixel is covered with a red, green, or blue color filter. Only red, green, or blue light components are able to pass through the red, green, and blue color filters, respectively. A light component produced by one of the color filters is made incident on the pixel that is covered by that color filter. Each pixel generates a pixel signal in accordance with the magnitude of the detected light component.

The image signal of one frame or one field comprises a plurality of pixel signals, generated by a plurality of pixels, and forming the entire image of one frame or one field captured by the imaging device 42.

The image signal generated by the imaging device 42 is sent to the image signal processing block 30 housed in the endoscope processor 20. The image signal processing block 30 carries out normal image processing, or emphasizing image processing, on the image signal so that a normal image, or an emphasized image, respectively, is displayed on the monitor 50. The normal image is the same as that of the captured image. The emphasized image is a partially-emphasized image of the normal image.

Figure 2:
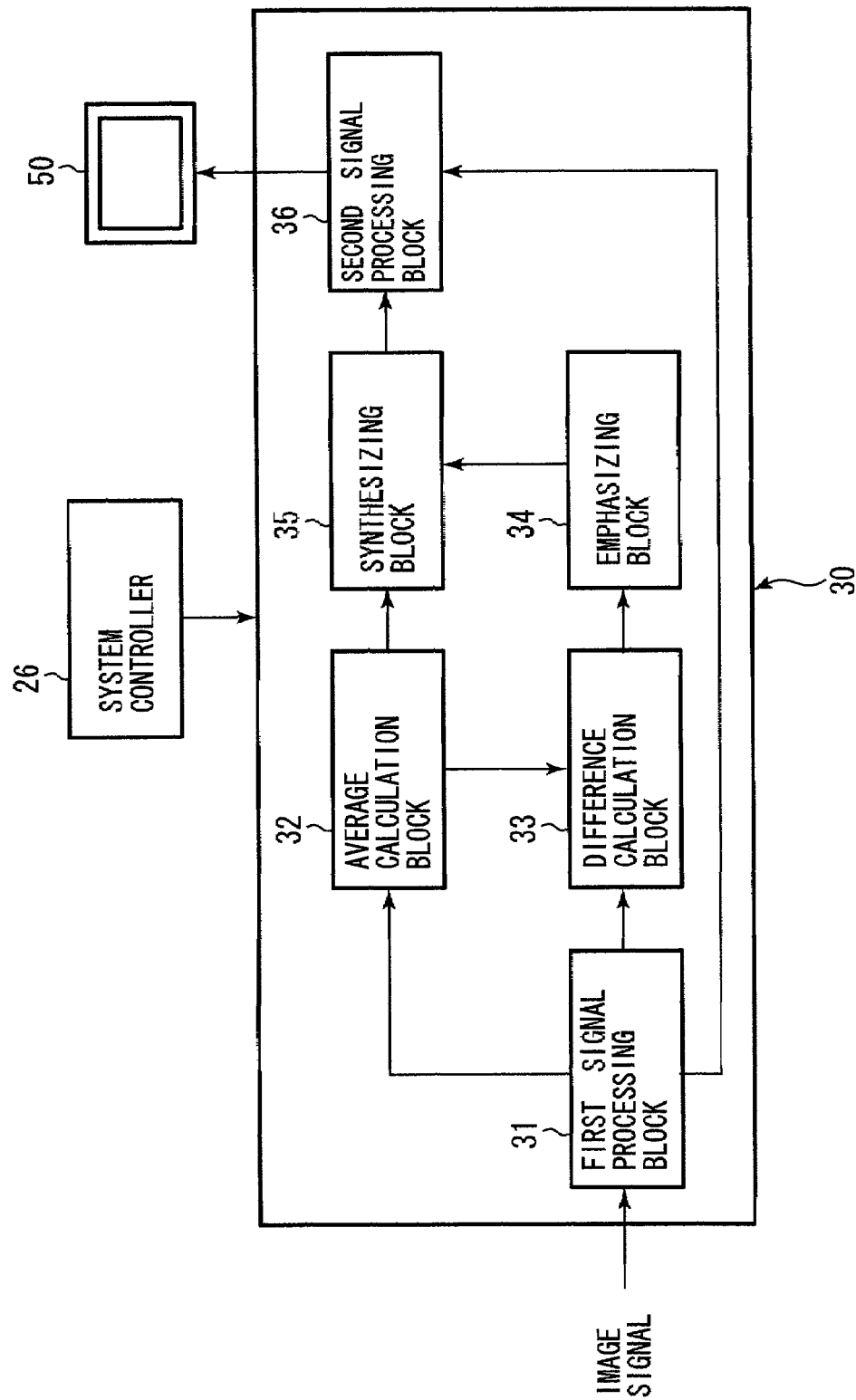
FIG. 2 is a block diagram showing the internal structure of the image signal processing block of the first embodiment.

As shown in FIG. 2, the image signal processing block 30 comprises a first signal processing block 31, an average calculation block 32, a difference calculation block 33, an emphasizing block 34, a synthesizing block 35, and a second signal processing block 36.

When the emphasizing image processing is carried out, the first signal processing block 31, the average calculation block 32, the difference calculation block 33, the emphasizing block 34, the synthesizing block 35, and the second signal processing block 36 function, as described later. On the other hand, when the normal image processing is carried out, only the first and second signal processing blocks 31, 36 function.

The image signal generated by the imaging device 42 is sent to the first signal processing block 31. The first signal processing block 31 carries out predetermined signal processing, which includes color separation processing and color interpolation processing.

In the color separation processing, the image signal is separated into red, green, and blue signal components, which are pixel signals categorized in accordance with their specific magnitude of red, green, and blue light components, respectively. At this point, each pixel signal consists of only one of the red, green, or blue color signal components, because each pixel can directly generate only one color signal component corresponding to its covering color filter.

During the color interpolation processing, in addition to the generated color signal component, two additional color signal components inherent within each pixel signal prior to the color interpolation processing, are synthesized. For example, in a pixel signal generated by a pixel covered with a green color filter and consisting of a green color signal component, the red and blue color signal components corresponding to the pixel are synthesized. Each pixel signal then consists of all three color signal components.

Further, the image signal, which is an analog signal, is converted to image data, which is digital data.

When normal image processing is carried out, the image data is sent from the first signal processing block 31 to the second signal processing block 36. When emphasizing image processing is carried out, the image data is sent from the first signal processing block 31 to the average calculation block 32 and the difference calculation block 33.

The average calculation block 32 receives red, green, and blue data components for each pixel that the image data comprises. Incidentally, the red, green, and blue data components are digital data converted from the red, green, and blue signal components, respectively. The data level of each color data component corresponds to the signal level of each color signal component.

The average calculation block 32 designates, one by one, all pixels as a focused pixel. In addition to the designation of the focused pixel, twenty four pixels that are arranged in five rows and five columns around the focused pixel are designated as surrounding pixels. The average calculation block 32 calculates a partial average value for a focused pixel. The partial average value is an average value of the data levels of data components for the focused pixel and the twenty four surrounding pixels.

Incidentally, the partial average value is separately calculated for the red, green, and blue data components. Accordingly, the partial average values corresponding to the red, green, and blue data components are referred to as the red, green, and blue partial average values, respectively. The data corresponding to the red, green, and blue partial average value for each pixel is sent to the difference calculation block 33 and the synthesizing block 35.

The difference calculation block 33 receives the image data also, as described above. The difference calculation block 33 calculates a red difference value for each pixel by subtracting the received red partial average value from each of the data levels of all the red data components. Similarly, the difference calculation block 33 calculates a green difference value for each pixel by subtracting the received green partial average value from each of the data levels of all the green data components. Similarly, the difference calculation block 33 calculates a blue difference value for each pixel by subtracting the received blue partial average value from each of all the data levels of the blue data components.

The data of the red, green, and blue difference values is sent to the emphasizing block 34. The emphasizing block 34 calculates red, green, and blue emphasized values for each pixel by multiplying the red, green, and blue difference values by a predetermined gain which is more than one.

The data of the red, green, and blue emphasized values is sent to the synthesizing block 35. The data of the red, green, and blue partial average values is also sent to the synthesizing block 35, as described above.

The synthesizing block 35 generates emphasized image data that corresponds to the emphasized image. The emphasized image data is generated based on the red, green, and blue emphasized values and the red, green, and blue partial average values. How the synthesized image data is generated is explained in detail below.

The synthesizing block 35 calculates the sum of the red partial average value and the red emphasized value for each pixel. The sum of the red partial average value and the red emphasized value is designated as the magnitude of the red light component for each pixel in the emphasized image. Similarly, the synthesizing block 35 calculates the sum of the green partial average value and the green emphasized value for each pixel. The sum of the green partial average value and the green emphasized value is designated as the magnitude of the green light component for each pixel in the emphasized image. Similarly, the synthesizing block 35 calculates the sum of the blue partial average value and the blue emphasized value for each pixel. The sum of the blue partial average value and the blue emphasized value is designated as the magnitude of the blue light component for each pixel in the emphasized image.

The emphasized image data is sent to the second signal processing block 36. The second signal processing block 36 carries out predetermined signal processing, such as contrast adjustment processing and enhancement processing, on the emphasized image data. In addition, D/A conversion processing is carried out on the emphasized image data, which is converted to an analog signal. Further, a composite video signal including the image signal and a synchronizing signal is generated.

Conversely, when normal image processing is carried out, the image data is sent from the first signal processing block 31 directly to the second signal processing block 36, which carries out the predetermined data processing on the received image data and generates the composite video signal corresponding to the normal image.

The composite video signal is sent to the monitor 50, where an image based on the composite video signal is displayed.

Figure 3:
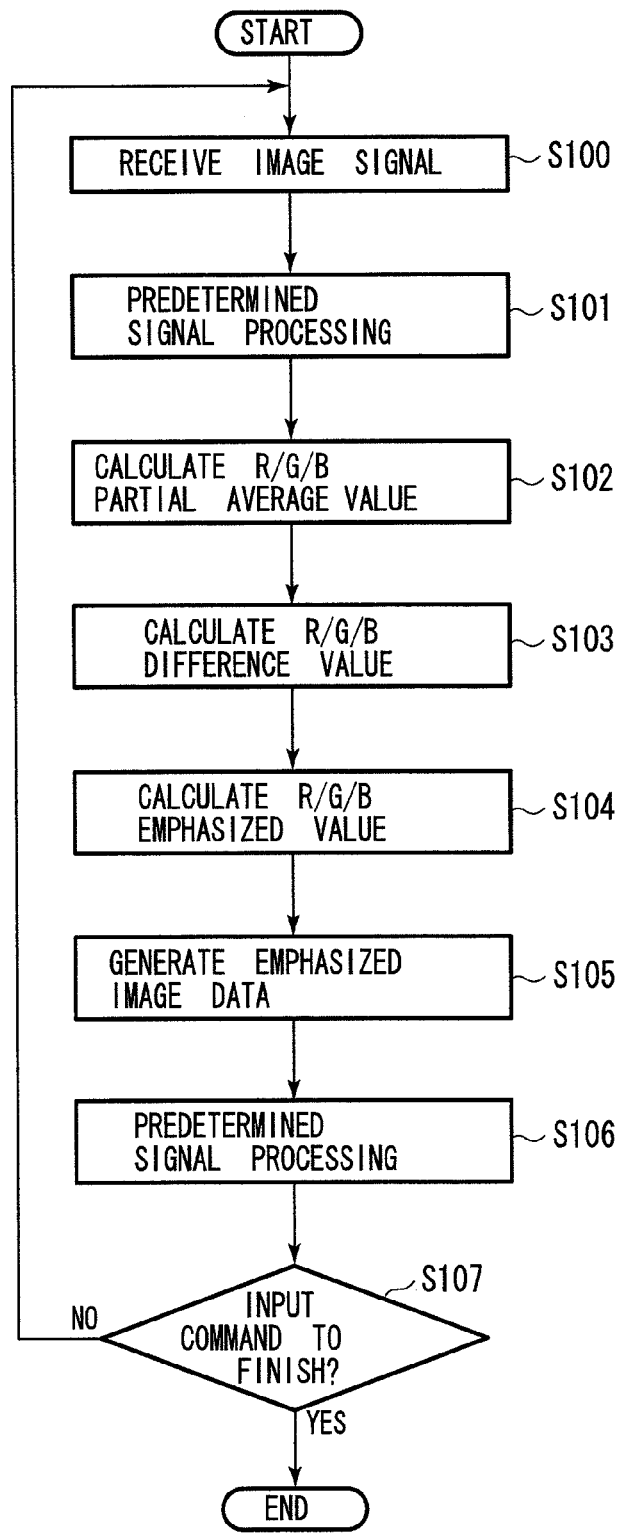
FIG. 3 is a flowchart describing the emphasizing image processing as carried out by the image signal processing block of the first embodiment.

The emphasizing image processing is carried out by the image signal processing block 30, as explained below using the flowchart in FIG. 3. The emphasizing image processing starts when a user inputs a command to start the emphasizing image process.

At step S100, the first signal processing block 31 receives one frame or one field of an image signal from the imaging device 42. At step S101, the first signal processing block 31 carries out predetermined signal processing, which includes a color separation processing and a color interpolation processing. Subsequently, red, green, and blue data components for each pixel are generated. After finishing the predetermined signal processing, the process proceeds to step S102.

At step S102, the average calculation block 32 calculates red, green, and blue partial average values based on the received image data. After the calculation of the partial average values, the process proceeds to step S103.

At step S103, the difference calculation block 33 calculates red, green, and blue difference values based on the average values calculated at step S102 and the data levels of red, green, and blue data components for each pixel. After calculation of the difference values, the process proceeds to step S104.

At step S104, the emphasizing block 34 calculates red, green, and blue emphasized values for each pixel by multiplying the red, green, and blue difference values by a predetermined gain. After the calculation of the emphasized values, the process proceeds to step S105.

At step S105, the synthesizing block 35 generates emphasized image data based on the red, green, and blue partial average values calculated at step S102 and the red, green, and blue emphasized values. In the emphasized image data, the sum of the red emphasized value for each pixel and the red partial average value is designated as the magnitude of the red light component for each pixel. Similarly, in the emphasized image data, the sum of the green emphasized value for each pixel and the green partial average value is designated as the magnitude of the green light component for each pixel. Similarly, in the emphasized image data, the sum of the blue emphasized value for each pixel and the blue partial average value is designated as the magnitude of the blue light component for each pixel. After generation of the emphasized image data, the process proceeds to step S106.

At step S106, the second signal processing block 36 carries out a predetermined signal process, including contrast adjustment processing and enhancement processing, on the emphasized image data and generates a composite video signal. The second signal processing block 36 sends the composite video signal to the monitor 50, where an image corresponding to the composite video signal is displayed.

At step S107, it is determined if there is an input command present to finish the emphasizing image processing. If there is an input command to finish the emphasizing image processing present, the emphasizing image process for the image signal finishes. If there is no such input command, the process returns to step S100. The processes from step S100 to step S107 are repeated until there is an input command detected to finish the emphasizing image processing.

In the above first embodiment, an unclear image can be converted into a clear image. Accordingly, a lesion that is not distinguishable in a normal image can be displayed clearly, as described below.

In the prior art, it is suggested to generate an emphasized image not based on the partial average value, but based on the average value of data components of the entire image. However, in such an emphasized image, a large amount of halation may be generated, or large areas may be colored completely black because the difference between the average value and the emphasized value is large. On the other hand, in the first embodiment, the difference value is rarely large because the difference value is the difference between the partial average value calculated using a focused pixel and its surrounding pixels, and data components of the focused pixel. Consequently, the areas where halation is generated, or which are colored completely black are reduced.

Next, an endoscope processor of the second embodiment is explained below. The primary difference between the second embodiment and the first embodiment, which is explained below, is the structure and function of the image signal processing block. Incidentally, the same index numbers are used for the structures that are comparable to those in the first embodiment.

Figure 4:
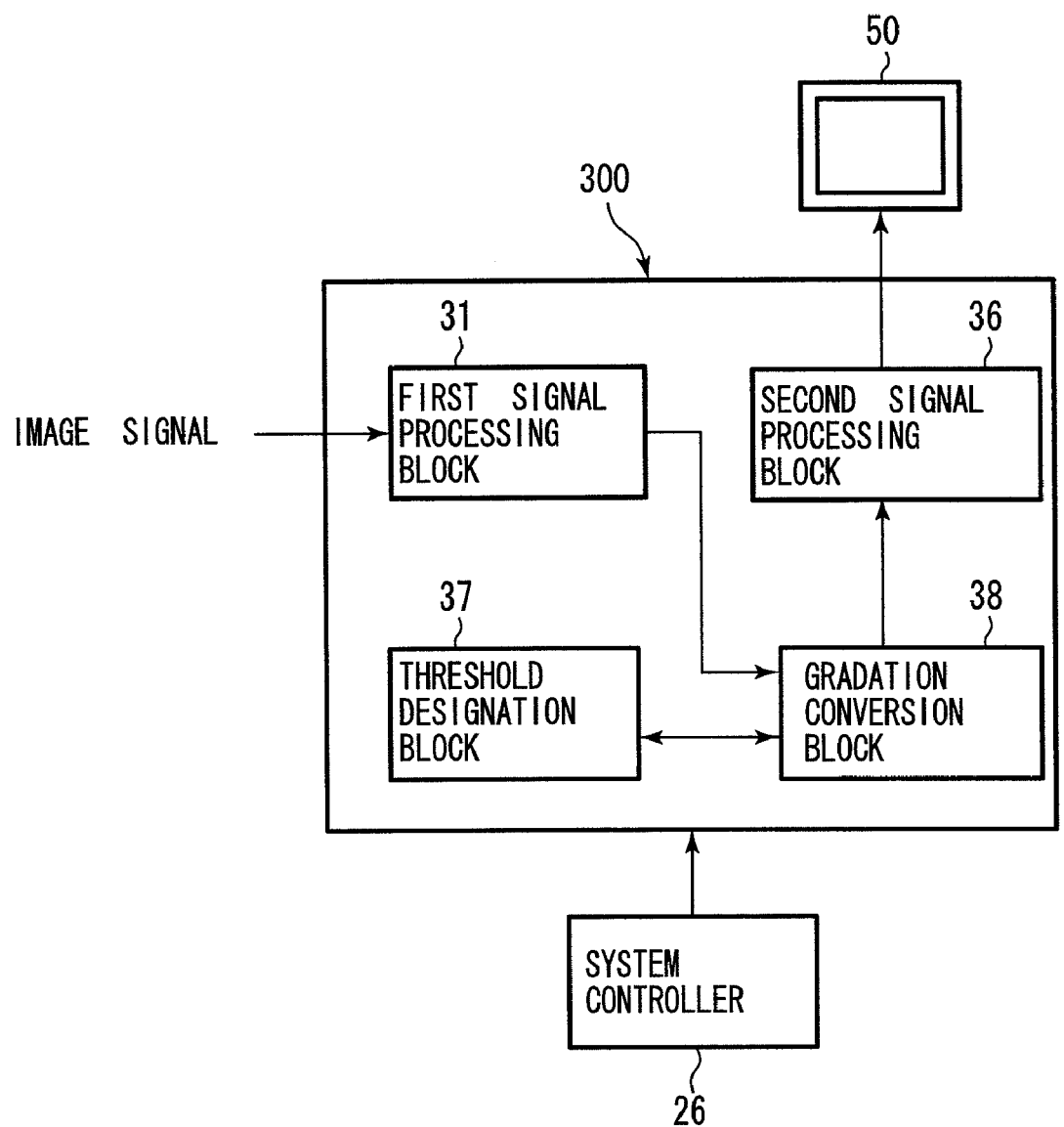
FIG. 4 is a block diagram showing the internal structure of the image signal processing block of the second embodiment.

As shown in FIG. 4, an image signal processing block 300 comprises a first signal processing block 31, a threshold designation block 37, a gradation conversion block 38, and a second signal processing block 36.

When the emphasizing image processing is carried out, the first signal processing clock 31, the threshold designation block 37, the gradation conversion block 38, and the second signal processing block 36 function, as described later. On the other hand, when the normal image processing is carried out, only the first and second signal processing blocks 31, 36 function, similar to the first embodiment.

The image signal generated by the imaging device 42 is sent to the first signal processing block 31, which carries out predetermined signal processing including color separation processing and color interpolation processing, on the received image data, similar to the first embodiment. In addition, the first signal processing block 31 converts the image signal, which is an analog signal, to image data, which is digital data with 256 gradations.

When the normal image processing is carried out, the image data is sent from the first signal processing block 31 to the second signal processing block 36, similar to the first embodiment. When the emphasizing image processing is carried out, the image data is sent from the first signal processing block 31 to the gradation conversion block 38.

The gradation conversion block 38 designates, one by one, all pixels as a focused pixel and converts 256 gradations of the red, green, and blue data components to 8 gradations of data components, described in detail below.

Incidentally, the lowest data level of the data components is referred to as the first gradation of the data components. The second lowest data level of the data components is referred to as the second gradation of the data components. The third lowest data level of the data components is referred to as the third gradation of the data components. The fourth lowest data level of the data components is referred to as the fourth gradation of the data components. The fifth lowest data level of the data components is referred to as the fifth gradation of the data components. The sixth lowest data level of the data components is referred to as the sixth gradation of the data components. The seventh lowest data level of the data components is referred to as the seventh gradation of the data components. The highest data level of the data components is referred to as the eighth gradation of the data components.

First, in addition to the designation of the focused pixel, the gradation conversion block 38 designates three hundred and ninety nine pixels that are arranged in twenty rows and twenty columns around the focused pixel as surrounding pixels. Data components corresponding to the focused pixel and the surrounding pixels are sent to the threshold designation block 37.

The threshold designation block 37 calculates an average value of the data levels of the received data components corresponding to the focused pixel and to the surrounding pixels as an initial threshold. Data corresponding to the initial threshold is sent to the gradation conversion block 38.

The gradation conversion block 38 compares the data level of the data component corresponding to the focused pixel and that of the surrounding pixels with the initial threshold. Based on this comparison, the gradation conversion block 38 categorizes the focused pixel and the surrounding pixels into either a first upper or first lower group. A pixel where the data level of the data component is less than the initial threshold is categorized into the first lower group. On the other hand, a pixel where the data level of the data component is more than the initial threshold is categorized into the first upper group. The group that the focused pixel is categorized into is designated as the first group.

Data components corresponding to the focused pixel and the surrounding pixels which are categorized into the first group are then sent to the threshold designation block 37.

The threshold designation block 37 calculates the average value of the data levels of the received data components corresponding to the focused pixel and the surrounding pixels, which are categorized into the first group, as a first threshold. Data corresponding to the first threshold is sent to the gradation conversion block 38.

The gradation conversion block 38 compares the data level of the data components corresponding to the focused pixel and the surrounding pixels, which are categorized into the first group, with the first threshold. Based on this comparison, the gradation conversion block 38 categorizes the focused pixel and the surrounding pixels into either a second upper or second lower group. A pixel where the data level of the data component is less than the first threshold is categorized into the second lower group. On the other hand, a pixel where the data level of the data component is more than the first threshold is categorized into the second upper group. The group that the focused pixel is categorized into is designated as the second group.

Data components corresponding to the focused pixel and the surrounding pixels which are categorized into the second group are then sent to the threshold designation block 37.

The threshold designation block 37 calculates the average value of the data levels of the received data components corresponding to the focused pixel and the surrounding pixels, which are categorized into the second group, as a second threshold. Data corresponding to the second threshold is sent to the gradation conversion block 38.

The gradation conversion block 38 compares the data level of the data component corresponding to the focused pixel with the second threshold. Based on this comparison, the gradation conversion block 38 categorizes the focused pixel into either a third upper or third lower group. A focused pixel where the data level of the data component is less than the second threshold is categorized into the third lower group. On the other hand, a focused pixel where the data level of the data component is more than the second threshold is categorized into the third upper group.

The gradation conversion block 38 sorts data into one of the 8 gradations of data components of the focused pixels, based on whether the focused pixel is categorized into the first lower or first upper group, the second lower or second upper group, and the third lower or third upper group. If the focused pixel is categorized into the first lower group, the data component of the focused pixel is sorted into one of the first-fourth gradations of data components. If the focused pixel is categorized into the first upper group, the data component of the focused pixel is sorted into one of the fifth-eighth gradations of data components. Next, if the focused pixel is also categorized into the second lower group, the data component of the focused pixel is sorted into one of the first, the second, the fifth, or the sixth gradations of data components. Conversely, if the focused pixel is also categorized into the second upper group, the data component of the focused pixel is sorted into one of the third, the fourth, the seventh, or the eighth gradations of data components. Next, if the focused pixel is also categorized into the third lower group, the data component of the focused pixel is converted to one of the first, the third, the fifth, and the seventh gradations of data components. Conversely, if the focused pixel is also categorized into the third upper group, the data component of the focused pixel is converted to one of the second, the fourth, the sixth, or the eighth gradations of data components.

Consequently, when the focused pixel is categorized into the first lower, the second lower, and the third lower groups, the data component of the focused pixel is sorted into the first gradation of data components among the eight gradations.

In addition, when the focused pixel is categorized into the first lower, the second lower, and the third higher groups, the data component of the focused pixel is sorted into the second gradation of data components among the eight gradations.

In addition, when the focused pixel is categorized into the first lower, the second higher, and the third lower groups, the data component of the focused pixel is sorted into the third gradation of data components among the eight gradations.

In addition, when the focused pixel is categorized into the first lower, the second higher, and the third higher groups, the data component of the focused pixel is sorted into the fourth gradation of data components among the eight gradations.

In addition, when the focused pixel is categorized into the first higher, the second lower, and the third lower groups, the data component of the focused pixel is sorted into the fifth gradation of data components among the eight gradations.

In addition, when the focused pixel is categorized into the first higher, the second lower, and the third higher groups, the data component of the focused pixel is sorted into the sixth gradation of data components among the eight gradations.

In addition, when the focused pixel is categorized into the first higher, the second higher, and the third lower groups, the data component of the focused pixel is sorted into the seventh gradation of data components among the eight gradations.

In addition, when the focused pixel is categorized into the first higher, the second higher, and the third higher groups, the data component of the focused pixel is sorted into the eighth gradation of data components among the eight gradations.

Incidentally, the conversion of 256 gradations to 8 gradations of data components is carried out separately for the red, green, and blue data components.

Finally, the gradation conversion block 38 generates emphasized image data corresponding to an emphasized image by the conversion of 256 gradations into 8 gradations of data components. Incidentally, the converted 8 gradations of red, green, and blue data components for each pixel correspond to the magnitude of red, green, and blue light components for each pixel in the emphasized image, respectively.

The emphasized image data is then sent to the second signal processing block 36. The second signal processing block 36 carries out predetermined signal processing for the emphasized image data, similar to the first embodiment. In addition, D/A conversion processing is carried out for the emphasized image data, which is then converted to an analog signal. Further, a composite video signal including the image signal and a synchronizing signal is generated.

Incidentally, when the normal image processing is carried out, the image data is sent from the first signal processing block 31 directly to the second signal processing block 36, which carries out predetermined data processing on the received image data and generates a composite video signal corresponding to the normal image, similar to the first embodiment.

The composite video signal is sent to the monitor 50, similar to the first embodiment. Finally, an image based on the composite video signal is displayed on the monitor 50.

Figure 5:
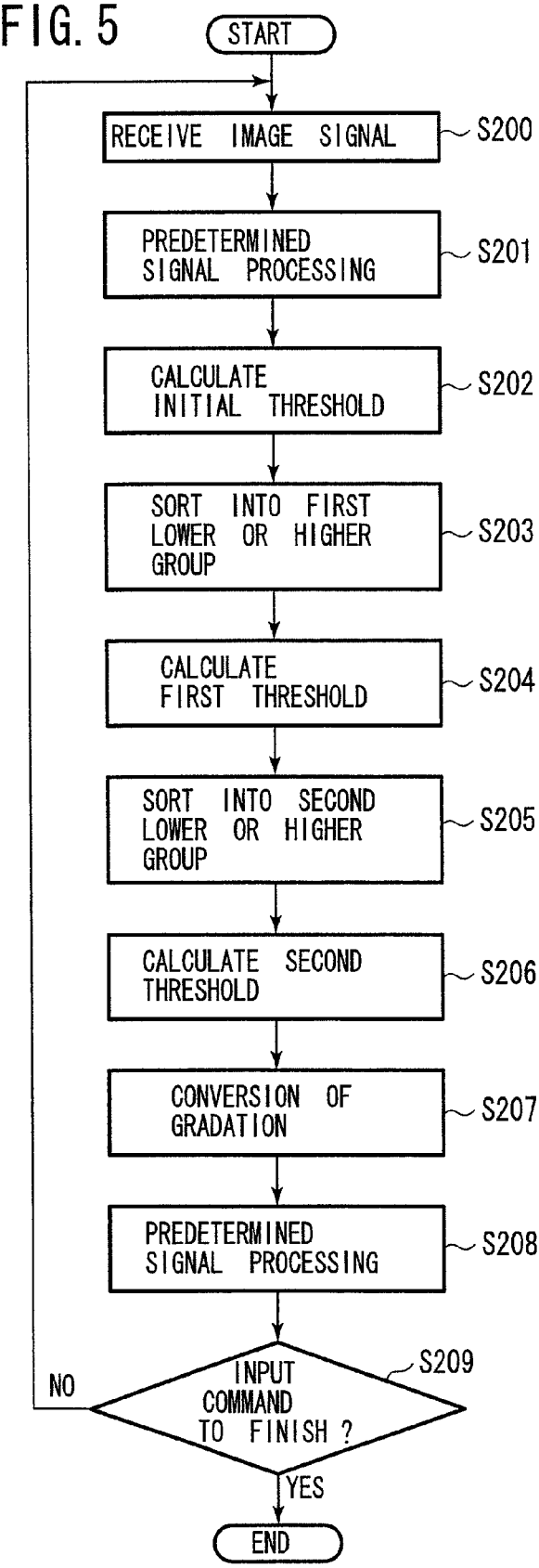
FIG. 5 is a flowchart describing the emphasizing image processing as carried out by the image signal processing block of the second embodiment.

The emphasizing image processing is carried out by the image signal processing block 300, as explained below using the flowchart in FIG. 5. The emphasizing image processing starts when a user inputs a command to start the emphasizing image processing.

At step S200, the first signal processing block 31 receives one frame or one field of an image signal from the imaging device 42. At step S201, the first signal processing block 31 carries out predetermined signal processing, which includes color separation processing and color interpolation processing. Red, green, and blue data components for each pixel are subsequently generated. After finishing the predetermined signal processing, the process proceeds to step S202.

At step S202, the threshold designation block 37, in cooperation with the gradation conversion block 38, calculates initial red, green, and blue thresholds based on the image data. After the calculation of the initial thresholds, the process proceeds to step S203.

At step S203, the gradation conversion block 38 sorts the focused pixel and the surrounding pixels into either the first lower or first upper group separately for each color component, based on the initial thresholds calculated at step S202. After this sorting, the process proceeds to step S204.

At step S204, the threshold designation block 37, in cooperation with the gradation conversion block 38, calculates first red, green, and blue thresholds based on the sorting at step S203. After the calculation of the first thresholds, the process proceeds to step S205.

At step S205, the gradation conversion block 38 sorts the focused pixel and the surrounding pixels into either the second lower or second upper group separately for each color component, based on the first thresholds calculated at step S204. After this sorting, the process proceeds to step S206.

At step S206, the threshold designation block 37, in cooperation with the gradation conversion block 38, calculates second red, green, and blue thresholds based on the sorting at step S205. After the calculation of the second thresholds, the process proceeds to step S207.

At step S207, the gradation conversion block 38 sorts the focused pixel into either the third lower or third upper group separately for each color component, based on the second thresholds calculated at step S206. In addition, the gradation conversion block 38 converts 256 gradations of red, green, and blue data components for the focused pixel into 8 gradations of red, green, and blue data components, based on the sorting at steps S203, S205, and S207. The gradation conversion block 38 generates the emphasized image data by converting the gradation of the red, green, and blue data components for all pixels. After the conversion, the process proceeds to step S208.

At step S208, the second signal processing block 36 carries out predetermined signal processing including contrast adjustment processing and enhancement processing, on the emphasized image data and generates a composite video signal. The second signal processing block 36 sends the composite video signal to the monitor 50, where an image corresponding to the composite video signal is displayed.

At step S209, it is determined if there is an input command to finish the emphasizing image processing. If there is an input command present to finish the emphasizing image processing, the emphasizing image processing for the image signal finishes. If there is no such input command, the process returns to step S200. The processes from step S200 to step S209 are repeated until there is an input command detected to finish the emphasizing image processing.

In the above second embodiment, it is possible to convert a normal image where an edge in the image is unclear, into an emphasized image where the unclear edge is sharpened. Accordingly, the image of an adenoma that cannot be clearly distinguished in the normal image, can be displayed clearly.

Figure 6:
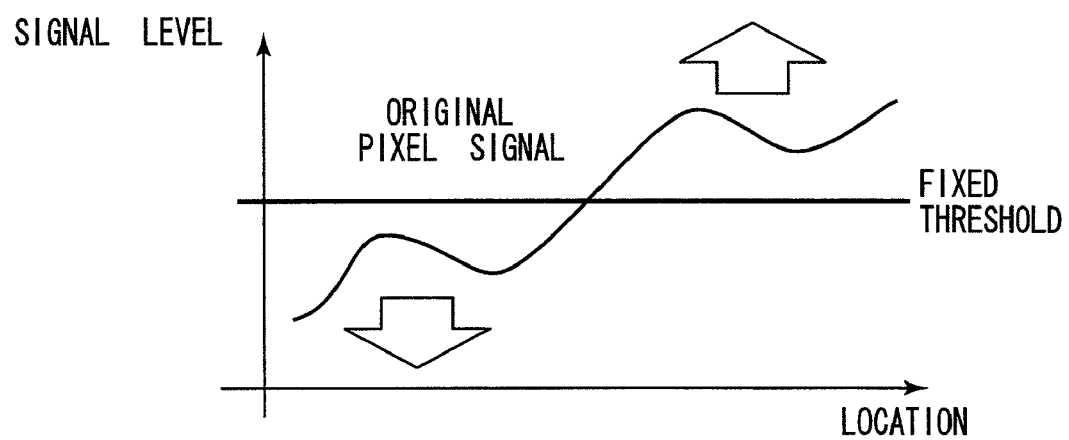
FIG. 6 is a diagram to explain the conversion of original pixel signals of pixels arranged in a line into decreased gradations based on a fixed threshold.

An emphasized image can be generated by converting 256 gradations of data components to a plurality of gradations of data components, such as 8, using a fixed threshold for all pixels in an entire image. However, in such a conversion, data components of neighboring pixels which are surely different, but both of which are higher than or lower than a fixed threshold, are sorted into the same gradation of data components (see FIG. 6). Consequently, the edge which should be shown by the two pixels does not appear.

Figure 7:
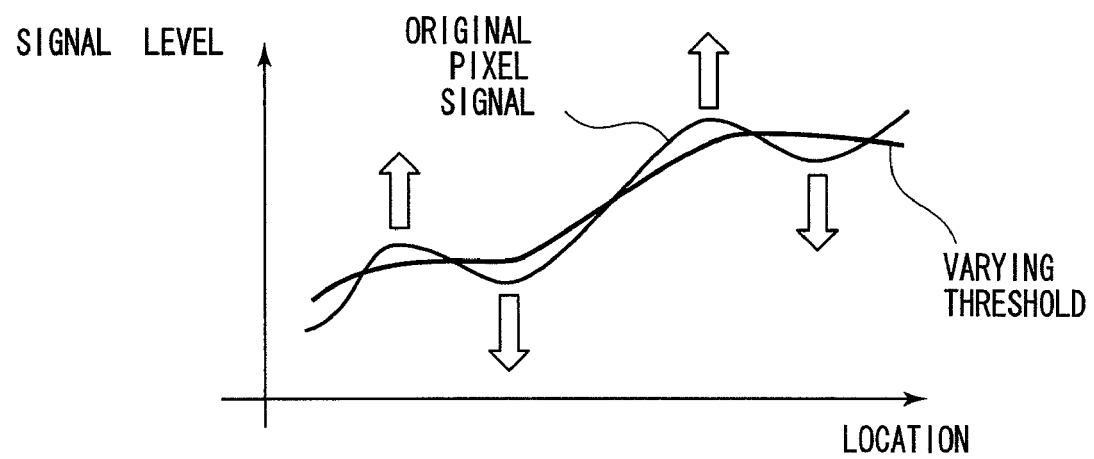
FIG. 7 is a diagram to explain the conversion of original pixel signals of pixels arranged in a line into decreased gradations based on a varying threshold in the second embodiment.

On the other hand, it is possible to use a threshold which alters according to the data levels of the surrounding pixels by calculating the threshold based on the average value of the data components generated by pixels in a partial area as for the above second embodiment (see FIG. 7). It is possible to sharpen an unclear edge that is in a dark or bright area by compressing the gradations of data components with such a varying threshold.

In the above first embodiment, the partial average value is calculated using red, green, and blue data components of each pixel and its surrounding pixels. This is a standard value, and the standard value is used for generating emphasized image data. In addition, in the above second embodiment, the initial, first, and second red, green, and blue threshold values are calculated using red, green, and blue data components of each pixel and its surrounding pixels as standard values, and the standard values are used for generating the emphasized image data. However, such a standard value, calculated using red, green, and blue data components may be used for any other signal processing.

In the above first embodiment, the partial average values, the difference values, and the emphasized values for all kinds of color, red, green, and blue data components are calculated and the emphasized image data is generated using the partial average values and the emphasized values. However, even if these values are calculated for at least one kind of color data component, and the emphasized image data is generated, the same effect is achieved as that of the first embodiment.

In the above second embodiment, 256 gradations of red, green, and blue data components are converted into 8 gradations of red, green, and blue data components, respectively and the emphasized image data is generated using the converted data components. However, even if such a conversion is carried out for at least one kind of color data component and the emphasized image data is generated, the same effect is achieved as that of the second embodiment.

In the above first and second embodiments, each pixel of the imaging device 42 is covered with either red, green, or blue color filters, and the emphasized image data is generated based on the red, green, and blue data components. However, each pixel may be covered with other kinds of color filter, and the emphasized image data may be generated based on a color data component corresponding to the color of the covering filter.

In the above first and second embodiments, the emphasized image data is generated based on the red, green, and blue data components. However, the emphasized image data can be generated based on other kinds of data components which can be used for produce of color in a captured image. For example, even if a luminance signal and a color difference signal are generated based on red, green, and blue signal components and the emphasized image data is generated based on a luminance signal and a color difference signal, the same effect can be achieved as those of the first and second embodiments.

In the above first embodiment, twenty four pixels surrounding a focused pixel are used for calculating the partial average value. In the above second embodiment, nine hundred and ninety nine pixels surrounding a focused pixel are used for calculating the initial, first, and second thresholds. However, any number of pixels surrounding a focused pixel can be used to calculate these.

In the above second embodiment, 256 gradations of a data component are converted into 8 gradations of a data component. However it is not limited to a conversion into 8 gradations. The same effect can be achieved as that of the second embodiment as long as an original gradation of data components is converted into a lower gradation.

In the above second embodiment, the number of gradations of data components of the image data before converting the gradation is 256. However, any number of gradations of the original image data are acceptable. The same effect can be achieved as that of the second embodiment as long as the original number of gradations before the conversion is greater than after the conversion.

The above first and second embodiments can be implemented by installing a program for emphasizing an image onto an all-purpose endoscope processor. The program for emphasizing an image comprises a controller code segment for receiving and a standard value calculation code segment.

In the above embodiment, the endoscope processor carries out signal processing on the image signal generated by the electronic endoscope, which comprises an insert tube to be inserted from an exterior. However, the endoscope processor can also carry out signal processing on an image signal generated by any other electronic endoscope, such as a capsule endoscope.

Furthermore, in the above embodiment, the endoscope processor receives the image signal, and carries out the above signal processing on the received image signal in real time. However, an endoscope image playback apparatus, which receives an image signal stored in internal or external memory, then carries out the above signal processing, including the emphasizing image processing, on the stored image signal while playing back the stored image.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2006-136691 (filed on May 16, 2006), which is expressly incorporated herein, by reference, in its entirety.

The invention claimed is:

1. An endoscope processor, comprising: a signal receiver that receives an image signal, said image signal being generated based on an optical image captured at a light receiving surface on an imaging device, said image signal comprising a plurality of pixel signals, said pixel signals being generated by a plurality of pixels according to amounts of received light, a plurality of said pixels being arranged on said light receiving surface on said imaging device; and a standard value calculator that calculates a standard value using a focused pixel signal and surrounding pixel signals, said focused pixel signal being said pixel signal of a focused pixel, said surrounding pixel signals being said pixel signals of surrounding pixels, said focused pixel being each said pixel designated one by one, said surrounding pixels surrounding said focused pixel, said standard value being used for carrying out signal processing on said focused pixel signal; and a signal processor that calculates a signal difference value which is the difference between the signal level of said focused pixel signal and said standard value, calculates an emphasized value by multiplying said signal difference value by a predetermined gain, and converts said image signal into an emphasized image signal by replacing said focused pixel signal with a signal corresponding to the sum of said standard value and said emphasized value, and said standard value being the average of the signal levels of said focused pixel signal and said surrounding pixel signals.

2. An endoscope processor according to claim 1, wherein, each of said pixels is covered with a first or second color filter, first and second said pixels covered with said first and second color filters generate first and second pixel signals, respectively, said standard value calculator calculates first and second standard values, said first and second standard values being said standard values corresponding to said first and second pixel signals, respectively, and said signal processor calculates first and second signal difference values, which are said signal difference values corresponding to said first and second pixel signals, respectively, calculates first and second emphasized values which are said emphasized values corresponding to said first and second pixel signals, and converts said image signal into said emphasized image signal by replacing first and second focused pixel signals with signals corresponding to the sum of said first and second standard values and said first and second emphasized values, respectively, said first and second focused pixel signals being said focused pixel signals corresponding to said first and second pixel signals, respectively.

3. An endoscope processor, comprising: a signal receiver that receives an image signal, said image signal being generated based on an optical image captured at a light receiving surface on an imaging device, said image signal comprising a plurality of pixel signals, said pixel signals being generated by a plurality of pixels according to amounts of received light, a plurality of said pixels being arranged on said light receiving surface on said imaging device; and a standard value calculator that calculates a standard value using a focused pixel signal and surrounding pixel signals, said focused pixel signal being said pixel signal of a focused pixel, said surrounding pixel signals being said pixel signals of surrounding pixels, said focused pixel being each said pixel designated one by one, said surrounding pixels surrounding said focused pixel, said standard value being used for carrying out signal processing on said focused pixel signal; and a signal processor that converts said image signal into an emphasized image signal by converting original gradations of said pixel signal into converted gradations based on said standard value, said original gradation being greater than $2^n$, said converted gradations being $2^n$, and said standard value being the average of the signal levels of said focused pixel signal and said surrounding pixel signals.

4. An endoscope processor according to claim 3, wherein said standard value calculator calculates an initial standard value which is an average of said focused pixel signal and said surrounding pixel signals that are generated by a predetermined number of said surrounding pixels, which are arranged at predetermined location relative to said focused pixel, said signal processor categorizes said focused pixel signal or said surrounding pixel signals whose signal level is lower or higher than said initial standard value, into a first lower or first higher group, respectively; said signal processor sorting the signal level of said focused pixel signal into one gradation between first and $2^{(n-1)}$st gradations when said focused pixel signal is categorized into said first lower group, and sorting said focused pixel signal into one gradation between $2^{(n-1)}+1$st and $2^n$th gradations when said focused pixel signal is categorized into said first higher group.

5. An endoscope processor according to claim 4, wherein said standard value calculator calculates a first standard value which is an average of said focused pixel signal and said surrounding pixel signals that are categorized into said first lower or first higher group with said focused pixel, said signal processor categorizes said focused pixel signal or said surrounding pixel signals whose signal level is lower or higher than said first standard value into a second lower or second higher group, respectively; said signal processor sorting the signal level of said focused pixel signal into one gradation between first and $2^{(n-2)}$st gradations in said first lower or first higher group when said focused pixel signal is categorized into said second lower group, and said signal processor sorting the signal level of said focused pixel signal into one gradation between $2^{(n-2)}+1$st and $2^{(n-1)}$st gradations in said first lower or first higher group when said focused pixel signal is categorized into said first higher group.

6. An endoscope processor according to claim 3, wherein each of said pixels is covered with a first or second color filter, first and second said pixels covered with said first and second color filters generate first and second pixel signals, respectively, said standard value calculator calculates first and second standard values, said first and second standard values being said standard values corresponding to said first and second pixel signals, respectively, and said signal processor converts said original gradations of said first and second pixel signals into said converted gradations based on said first and second standard values, respectively.

7. A non-transitory computer readable medium storing a computer program product, said computer program product comprising: a controller that activates a signal receiver so that said signal receiver receives an image signal, said image signal being generated based on an optical image captured at an light receiving surface on an imaging device, said image signal comprising a plurality of pixel signals, said pixel signals being generated by a plurality of pixels according to amounts of received light, a plurality of said pixels being arranged on said light receiving surface on said imaging device; and a standard value calculator that calculates a standard value using a focused pixel signal and surrounding pixel signals, said focused pixel signal being said pixel signal of a focused pixel, said surrounding pixel signals being said pixel signals of surrounding pixels, said focused pixel being said each pixel designated one by one, said surrounding pixels surrounding said focused pixel, said standard value being used for carrying out signal processing on said focused pixel signal;

and a signal processor that calculates a signal difference value which is the difference between the signal level of said focused pixel signal and said standard value, calculates an emphasized value by multiplying said signal difference value by a predetermined gain, and converts said image signal into an emphasized image signal by replacing said focused pixel signal with a signal corresponding to the sum of said standard value and said emphasized value, and said standard value being the average of the signal levels of said focused pixel signal and said surrounding pixel signals.

8. An endoscope system, comprising: an endoscope that has an imaging device, said imaging device generating an image signal based on an optical image captured at an light receiving surface, said image signal comprising a plurality of pixel signals, said pixel signals being generated by a plurality of pixels according to amounts of received light, a plurality of said pixels being arranged on said light receiving surface on said imaging device; and a standard value calculator that calculates a standard value using a focused pixel signal and a surrounding pixel signal, said focused pixel signal being said pixel signal of a focused pixel, said surrounding pixel signals being said pixel signals of surrounding pixels, said focused pixel being said each pixel designated one by one said surrounding pixels surrounding said focused pixel, said standard value being used for carrying out signal processing on said focused pixel signal;

and a signal processor that calculates a signal difference value which is the difference between the signal level of said focused pixel signal and said standard value, calculates an emphasized value by multiplying said signal difference value by a predetermined gain, and converts said image signal into an emphasized image signal by replacing said focused pixel signal with a signal corresponding to the sum of said standard value and said emphasized value, and said standard value being the average of the signal levels of said focused pixel signal and said surrounding pixel signals.

* * * * *